United States Patent [19]

Schlegel

[11] Patent Number: 4,863,466

[45] Date of Patent: Sep. 5, 1989

[54] INTRA-OCULAR IMPLANT LENS

[76] Inventor: Hans-Joachim Schlegel, Siebenpfeifferstrasse 22, 6650 Homburg/Saar, Fed. Rep. of Germany

[21] Appl. No.: 138,494

[22] Filed: Nov. 27, 1987

[30] Foreign Application Priority Data

Apr. 1, 1986 [DE] Fed. Rep. of Germany ....... 3610833
Apr. 1, 1987 [WO] PCT Int'l Appl. ... PCT/DE87/00142

[51] Int. Cl.$^4$ ............................................. A61F 2/16
[52] U.S. Cl. ...................................... 623/6; 351/161; 351/162
[58] Field of Search .................... 623/6; 351/160-162

[56] References Cited

U.S. PATENT DOCUMENTS

| 4,010,496 | 3/1977 | Neefe ........................................ 623/6 |
| 4,102,567 | 7/1978 | Cuffe et al. ...................... 623/6 UX |
| 4,172,297 | 10/1979 | Schlegel ................................... 623/6 |
| 4,210,391 | 7/1980 | Cohen ................................. 351/161 |
| 4,424,597 | 1/1984 | Schlegel ................................... 623/6 |
| 4,636,212 | 1/1987 | Posin ....................................... 623/6 |

FOREIGN PATENT DOCUMENTS

| 3428895 | 2/1986 | Fed. Rep. of Germany .......... 623/6 |
| 2124500A | 2/1984 | United Kingdom .................... 623/6 |

Primary Examiner—Ronald L. Frinks
Attorney, Agent, or Firm—Nies, Webner, Kurz & Bergert

[57] ABSTRACT

Intra-ocular implant lens (11) in which is embedded a transparent, tinted plastic disc (15).

9 Claims, 1 Drawing Sheet

INTRA-OCULAR IMPLANT LENS

This is a continuing application, under the provisions of Title 35 U.S.C., Sections 365 (a) and (b), and 120, of International application PCT/DE87/00142 with an international filing date of Apr. 1, 1987 and a German application priority date of Apr. 1, 1986.

The invention refers to an intra-ocular implant lens with a central lens body designed as a converging lens, said lens body having a holder extending radially in an outward direction to support and center the lens in the eye, consisting of a flexible, elastic plastic, particularly a vulcanized silicone material, and being constituted so as to be foldable for the implantation.

Lenses of the type in question serve as replacements for the lens, clouded by a cataract, which has been surgically removed from the eye of living beings, particularly humans. Such artificial lenses are generally crystal clear and permeable to rays of visible light with a wavelength of approximately 400 to approximately 800 nm and rays in the ultraviolet range with a wavelength of approximately 280 to approximately 400 nm.

Older or aged patients with an implanted artificial lens of the type in question frequently complain of post-operative glare, which is quite understandable since the surgically removed natural lens had a yellow coloring caused by age, whereas the implanted lens is crystal clear.

The invention is therefore based on the task of creating an implant lens of the type in question, consisting on the one hand of an elastic, flexible material which has proven to be biocompatible and chemically inert, and on the other hand being adjusted with regard to color such that it approximately corresponds to that of the healthy, aged eye while the transparency is maintained. Furthermore, an additional task consists in designing such lenses to be able to absorb ultraviolet rays at least to an extent considered necessary.

For the solution of this task, in accordance with the invention it is proposed that the intra-ocular implant lens be designed in such a way that a transparent disc tinted to a yellow-brown shade of color approximately corresponding to that of the natural lens resulting from progressive yellowing, is embedded in the lens material and is hence completely enclosed by the material forming the lens so that it can not come into contact anywhere with the aqueous humor surrounding the lens. In this way, the age-conditioned color perception of the surgically treated eye is restored to approximately correspond to that of a healthy eye.

If, on the other hand, the substances used for the desired tinting of the lenses were mixed with the material of which the lenses are made, this would have the considerable disadvantage that the substances in question would be homogenously distributed in the molecular structure of the plastic material and thus would also be subject to the influence of the aqueous humor on the lens surface, so that undesired chemical and biochemical reactions could take place and it would be possible for these substances to extract themselves from the molecular structure of the material.

However, since the action of ultraviolet rays on the retina is also undesirable, as a supplement it is further proposed in particular that the disc embedded in the lens material be additionally rendered impermeable to UV rays at least for the most part.

Substances absorbing UV rays have already been added to the material of polymethyl methacrylate implant lenses, so that with regard to such lenses and to lenses tinted as mentioned above, the aforesaid shortcomings must be particularly feared. Even though such findings could not yet be made in short-term observations up to now, experience shows that in the long run such processes must be expected nonetheless. Experiences made in implant surgery on the eye show that substances originally considered to be biochemically inert and therefore indestructable, such as polyamides or polypropylene or the like, decayed within the eye with the passage of time and, moreover, became toxic products of decomposition. This resulted in a substantial number of such implant lenses having to be removed from the surgically treated eye. This leads to the realization that it is extremely dangerous to implant such lenses, which do not behave chemically and biochemically in an absolutely neutral manner in the eye of living beings.

If one proceeds as suggested, flexible, foldable or rollable lenses particularly well-suited for a special, promising surgical method are obtained, with regard to which absolute compatability is guaranteed.

Additional features of the implant lens designed in accordance with the invention are to be found in the subclaims and the following description of two preferred embodiments shown in FIGS. 1 to 5 of the drawings, which are described in more detail below.

Figure 1:
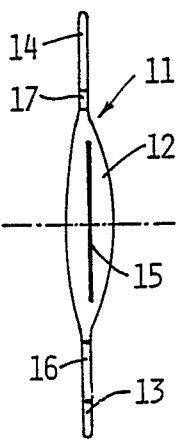
FIG. 1 shows a longitudinal section through an implant lens with biconvex lens body, with a disc containing a ray-absorbent substance embedded in its material.
Figure 2:
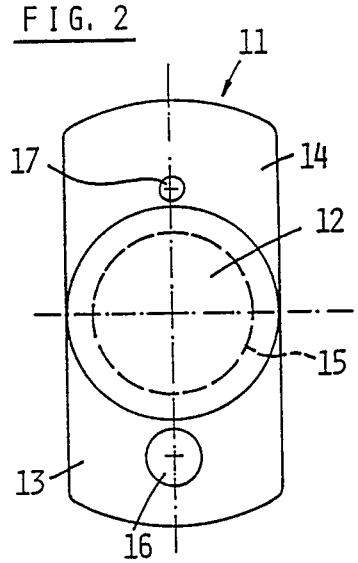
FIG. 2 shows a plan view of the implant lens according to FIG. 1.

The lens 11 shown in FIGS. 1 and 2 has a basically known form. It has a central, biconvex lens body 12, with diametrically opposed support tabs 13 and 14 extending radially outwardly or up and down, and having a thickness which is slight but adequately dimensioned to hold the implanted lens 11 in its position in the eye. This lens 11 consists advantageously of a vulcanized silicone material with a Shore hardness of 30 to 50, but preferably approximately 35 to 45, so that it has good elasticity and flexibility with sufficient stability.

A flexible disc 15, preferably likewise consisting of vulcanized silicone material or if applicable a material chemically related to it, is embedded in the material of the lens 11, in the central area of the lens body 12. This material contains a preferably yellow-brownish dye on the one hand, and a substance absorbing UV rays in the range of approximately 280 nm to approximately 400 nm on the other. For practical purposes this disc 15 is disposed in the central plane of the implant lens 11 or somewhat behind it in the direction of the light penetration; the latter is more advantageous for the path of the rays and the shielding, as the disc 15 must be somewhat smaller in diameter, advantageously approximately 10 to 15% smaller than the central, optically effective lens body 12.

In the lower support tab 13 there is an opening 16 serving the widest variety of purposes. In particular, aqueous humor can pass through it. In the upper support tab 14 there is a relatively small opening 17 serving to receive the tip of an inserting instrument used in the implantation, by means of which the conventional operation is simplified and facilitated.

The one opening 16 has a diameter which is approximately ¼ of the width of the holders 13 and 14 and the relatively small opening 17 has a diameter which is approximately 1/10 of the width of the holders 13 and 14.

Figure 3:
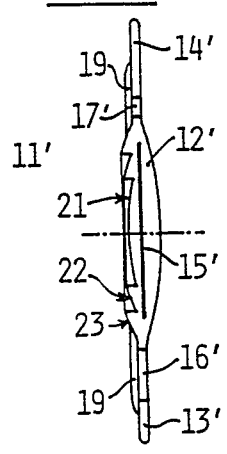
FIG. 3 shows a longitudinal section through an implant lens with its lens body designed as a modified fresnel lens.
Figure 4:
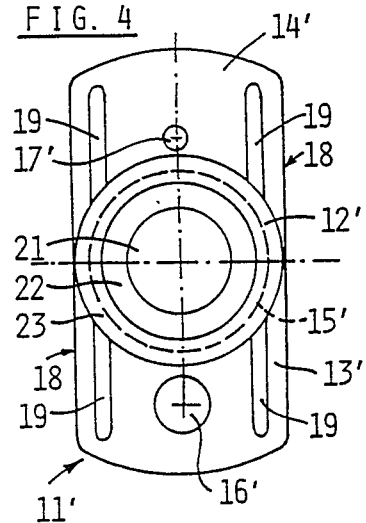
FIG. 4 shows a plan view of the lens according to Figure 3.

The lens 11' according to FIGS. 3 and 4 practically corresponds to the one according to FIGS. 1 and 2. It differs from it merely in that the central lens body 12' is designed as a fresnel lens, in this case, for example, as a one-sided three-step fresnel lens in which the steps are preferably located on the back of the lens body 12'. Located radially on the outside of the central, convex surface 21 are the annular lens steps 22 and 23 with correspondingly convex surfaces.

The elastic, flexible implant lenses 11 and 11' described above offer the advantage that they can be simply and easily folded or rolled up for insertion into the eye and therefore require only an unusually small incision of approximately 3 to 4 mm in length during surgery. An implant lens of the second type according to FIGS. 3 and 4 is more advantageous in this respect, as it does not have the thickness of a biconvex lens 12 in the central, optically effective area 12', so that its foldability or rollability is especially good.

In order to design the support tabs 13 and 14 and/or 13' and 14' to be equally as foldable or rollable in the longitudinal direction as they are sufficiently buckle-proof in the transverse direction, two bulge-like stiffener ribs 19 are located on the support tabs 13' and 14', parallel to the two straight side edges 18 of the lens 11', as FIGS. 3 and 4 show as examples. These can be provided either only on the front side or only on the back side of the lens 11', or also on both sides. These ribs 19 can be provided correspondingly in the lens 11 according to FIGS. 1 and 2.

Figure 5:
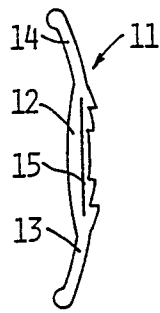
FIG. 5 shows a longitudinal section through an implant lens with curved support tabs.

The implant lens according to the invention can also preferably have a form such as that seen for example in FIG. 5.

I claim:

1. A one-piece, homogeneous intra-ocular implant lens with a central lens body designed as a converging lens, said lens body having one holder on each of two diametrically opposed sides, said holders extending radially in an outward direction to support and center the lens in the eye, consisting of a flexible, elastic plastic, particularly a vulcanized silicone material, and being constituted so as to be foldable for the implantation, characterized in that a transparent disc (15) tinted to a yellow-brownish shade of color and made of a flexible plastic foil is embedded in the material of the lens (11).

2. An implant lens according to claim 1, characterized in that the plastic foil disc (15) embedded in the material of the lens (11) consists of the same material as the lens itself or of a chemically related material.

3. An implant lens especially according to claim 1 characterized in that the the plastic foil disc (15) embedded in the material of the lens (11) contains a substance at least mostly absorbing ultraviolet rays with a wavelength of approximately 280 nm to approximately 400 nm.

4. An implant lens according to claim 1, characterized in that the plastic foil disc (15) is disposed behind the central plane of the lens (11) in the direction of the light penetration.

5. An implant lens according to claim 1 characterized in that the plastic foil disc (15) is approximately 10 to 15% smaller in diameter than the central, optically effective lens body (12).

6. An implant lens according to claim 5 characterized in that the lens body (12) is a biconvex converging lens.

7. An implant lens according to claim 5 characterized in that the lens body (12') is a two-step, three-step or multistep fresnel lens.

8. An implant lens according to claim 6, characterized in that one opening (16, 17) is located in each of the two opposite holders (13, 14) extending radially toward the outside, with the one opening (16) having a diameter of approximately ¼ and the other opening (17) having a diameter of approximately 1/10 of the width of the holder (13, 14).

9. An implant lens according to claim 8 characterized in that the two opposite holders (13, 14) extending radially toward the outside have at least two bulge-like ribs (19) parallel to the axis or edge, on their front and/or back side.

* * * * *